US006337208B1

(12) United States Patent
Graupner

(10) Patent No.: US 6,337,208 B1
(45) **Date of Patent: *Jan. 8, 2002**

(54) CLONING VECTOR

(76) Inventor: Stefan Graupner, Zanderweg 15, 21627 Oldenburg (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/476,366

(22) Filed: Jan. 3, 2000

(51) Int. Cl.[7] .................... C12N 15/00; C12N 15/74; C12Q 1/68; C12P 21/01; A01N 63/00

(52) U.S. Cl. .................... 435/320.1; 435/4; 435/6; 435/69.1; 435/91.1; 435/71.2; 435/252.1; 424/93.21; 424/94.61; 536/23.2; 536/23.7; 536/24.1

(58) Field of Search .................... 435/4, 6, 69.1, 435/91.1, 71.2, 252.1, 320.1, 471; 424/93.21, 94.61; 536/23.2, 23.7, 24.1

(56) References Cited

U.S. PATENT DOCUMENTS 5,830,690 A * 11/1998 Gowrishankar et al. ... 435/69.1
5,955,258 A * 9/1999 Buist et al. .................... 435/4
6,077,687 A * 6/2000 Grieve et al. .............. 435/69.1

OTHER PUBLICATIONS

Yanisch Perron et al., "Improved M13 phage cloning vectors and host strains: nucleotide sequence of the M13amp 18 and pUC19 vectors", Gene, vol. 33, pp. 103–119, 1985.*

Hayes, P.K., "The gvp operon of Anabaena flos–aquae has multiple copies of a GVPa encoding gene; Expression of the genes in *Escherichia coli* is lethal", GenBank Accession No., M32060, Nov. 1995.*

Stratagene Catalog, "Gene Characterization Kits", p. 39, 1988.*

Hayes et al., "The gvpA/C cluster of Anabaena flos–aquae has multiple copies of a gene encoding GvpA", Arch. Microbiol. 164:50–57, 1995.*

Geider et al., "Influence of fd gene . . . ", Nucleic Acids Research, vol. 16 (14)., 6385–6396, 1988.

* cited by examiner

*Primary Examiner*—W. Gary Jones
*Assistant Examiner*—Arun Kr. Chakrabarti
(74) *Attorney, Agent, or Firm*—Arent Fox Kintner Plotkin & Kahn, PLLC

(57) ABSTRACT

The present invention relates to cloning vectors, cloning methods and cloning kits. More particularly, the present invention relates to a cloning vector comprising a nucleic acid sequence encoding a polypeptide which when expressed is lethal for a bacterial host cell and at least one cloning site wherein the insertion of a foreign nucleic acid insert in the cloning site causes a disruption of the expression of the lethal polypeptide.

19 Claims, 1 Drawing Sheet

SEQUENCE LISTING

```
<160> NUMBER OF SEQ ID NOS: 4

<210> SEQ ID NO 1
<211> LENGTH: 4490
<212> TYPE: DNA
<213> ORGANISM: Artificial Sequence
<220> FEATURE:
<223> OTHER INFORMATION: Description of Artificial Sequence: vector
      pCorrectClone including modified gvpA sequence from Anabaena
      flos-aquae
<221> NAME/KEY: CDS
<222> LOCATION: (251)..(505)
<221> NAME/KEY: Misc _ Feature
<222> LOCATION: (1009) ..(1009)
<223> OTHER INFORMATION: The n at position 1009 can be A, T, C or G
<221> NAME/KEY: Misc _ Feature
<222> LOCATION: (2223)..(2223)
<223> OTHER INFORMATION: The n at position 2223 can be A, T, C or G

<400> SEQUENCE: 1

gcgccggtga tgccggccac gatgcgtccg gcgtagagga tctctcacct accaaacaat     60

gcccccctgc aaaaaataaa ttcatataaa aaacatacag ataaccatct gcggtgataa    120

attatctctg gcggtgttga cataaatacc actggcggtg atactgagca catcagcagg    180

acgcactgac caccatgaag gtgacgctct taaaattaag ccctgattaa ctttataagg    240

aggatatacc atg ggt acc ccg ggt gaa ttc gat atc tcg agc ggc cgc       289
           Met Gly Thr Pro Gly Glu Phe Asp Ile Ser Ser Gly Arg
             1               5                  10

gtc gac gca gtt gaa aaa acc aat tct tcc tcc agc ttg gca gaa gtt      337
Val Asp Ala Val Glu Lys Thr Asn Ser Ser Ser Ser Leu Ala Glu Val
     15                  20                  25

att gat aga atc ctc gac aaa ggt atc gta att gac gct tgg gtt cgt      385
Ile Asp Arg Ile Leu Asp Lys Gly Ile Val Ile Asp Ala Trp Val Arg
 30                  35                  40                  45

gtt tcc tta gtt ggt atc gaa cta cta gca att gaa gct cgg atc gtt      433
Val Ser Leu Val Gly Ile Glu Leu Leu Ala Ile Glu Ala Arg Ile Val
                50                  55                  60

atc gct tcc gtt gaa acc tac ttg aag tat gct gaa gca gtt ggt ttg      481
Ile Ala Ser Val Glu Thr Tyr Leu Lys Tyr Ala Glu Ala Val Gly Leu
             65                  70                  75

acc caa tca gca gca gta cct gct taatttaatt aagctccata atatcaggat     535
Thr Gln Ser Ala Ala Val Pro Ala
         80                  85

taattaatcc tgatattggt tctgcttttt ttaaaagggc agcattcaaa gcagaaggct    595

ttggggtgtg tgatacgaaa tgaagctttg gaattcacct cgaaagcaag ctgataaacc    655

gatacaatta aaggctcctt ttgccaagct gagccttttt ttttggagat tttcaacgtg    715

aaaaaattat tattcgcaat taattcacct cgaaagcaag ctgataaacc gatacaatta    775

aaggctcctt ttgccaagct gagccttttt ttttggagat tttcaacgtg aaaaaattat    835

tattcgcaat ccaagctgcc tcgcgcgttt cggtgatgac ggtgaaaacc tctgacacat    895

gcagctcccg gagacggtca cgcttgtctg taagcggatg ccgggagcag acaagcccgt    955
```

-continued

```
cagggcgcgt cagcgggtgt tggcgggtgt cggggcgcag ccatgaccaa ttcnaacatc   1015
caataaatcg tacaagcaag gcagagagtt agcaaaatta agcaataaag cctcagagca   1075
taaagctaaa tcggttgtac caaaaacatt atgaccctgt aatacttttg ctggtgaagc   1135
cttaatttca acgcagggat aaaaattttt agaaccctca tatattttaa atgcaatgcc   1195
ggagtaatga gtaggcaaag attcaaacgg gtgagaaagg ccggagacag tcaaatcacc   1255
gtcaatatga tattcaaccg ttctagctga taaattcatg ccggagaggg tagctatttt   1315
tgagaggtct acaaaggcta tcaggtcatt acctgaaagt ctggagcaaa caagagaatc   1375
gatgaacggt aatcgtaaaa ctagcatgtc aatcatatgt accccggttg ataatcagaa   1435
aagccccaaa aacaggatga ttgtataagc aaatatttaa attgtaaacg ttaatgtttt   1495
gttaaatttc gcgttaaata tttgttaaat cagcttattt tttaaccagt aagcagaaaa   1555
tgacaaaaat ccttataaat caaaagaata ggccgagtta gttgtgagtg ttgttccagt   1615
ttggaacaag agtccactat taaagaacgt ggactccaac gtcaaagggc gaaaaaccgt   1675
ctatcagggc gatggcccac tacgtgaacc atcaccctaa tcaagttttt tggggtcgag   1735
gtgccgtaaa gcactaaatc ggaaccctaa agggagcccc cgatttagag cttgacgggg   1795
aaagccggcg aacgtggcga gaaaggaagg gaagaaagcg aaaggagcgg gcgctagggc   1855
gctggcaagt gtagcggtca cgctgcgcgt aaccaccaca cccgccgcgc ttaatgcgcc   1915
gctacagggc gcgtactatg gttgctttga cgagcacgta caacgtgctt tcctcgttag   1975
aatcagaacg ggagctaaac aggaggccga ttaaagggat tttagacagg aacggcacac   2035
cagaatcttg agaagtgttt ttgtaatcag tgaggccacc gagcaaaaga gtctgaccat   2095
cacgcaaatt aaccgttgtc gcaatacttc tttgattagt aataacatca cttgcctgag   2155
tagaagaact caaactatcg gccttactgg ttatatctaa aacaatatta ccgccagcca   2215
ttgcaaanga attaattcca gtcacgtagc gatagcggag tgtatactgg cttaactatg   2275
cggcatcaga gcagattgta ctgagagtgc accatatgcg gtgtgaaata ccgcacagat   2335
gcgtaaggag aaaataccgc atcaggcgct cttccgcttc ctcgctcact gactcgctgc   2395
gctcggtcgt tcggctgcgg cgagcggtat cagctcactc aaaggcggta atacggttat   2455
ccacagaatc aggggataac gcaggaaaga acatgtgagc aaaaggccag caaaaggcca   2515
ggaaccgtaa aaaggccgcg ttgctggcgt ttttccatag gctccgcccc cctgacgagc   2575
atcacaaaaa tcgacgctca agtcagaggt ggcgaaaccc gacaggacta taaagatacc   2635
aggcgtttcc ccctggaagc tccctcgtgc gctctcctgt tccgaccctg ccgcttaccg   2695
gatacctgtc cgcctttctc ccttcgggaa gcgtggcgct ttctcaatgc tcacgctgta   2755
ggtatctcag ttcggtgtag gtcgttcgct ccaagctggg ctgtgtgcag caaccccccg   2815
ttcagcccga ccgctgcgcc ttatccggta actatcgtct tgagtccaac ccggtaagac   2875
acgacttatc gccactggca gcagccactg gtaacaggat tagcagagcg aggtatgtag   2935
gcggtgctac agagttcttg aagtggtggc ctaactacgg ctacactaga aggacagtat   2995
ttggtatctg cgctctgctg aagccagtta ccttcggaaa aagagttggt agctcttgat   3055
ccggcaaaca aaccaccgct ggtagcggtg gtttttttgt ttgcaagcag cagattacgc   3115
gcagaaaaaa aggatctcaa gaagatcctt tgatcttttc tacggggtct gacgctcagt   3175
ggaacgaaaa ctcacgttag ggattttggt catgagatta tcaaaaagga tcttcaccta   3235
gatcctttta aattaaaaat gaagttttaa atcaatctaa agtatatatg agtaaacttg   3295
```

-continued

```
gtctgacagt taccaatgct taatcagtga ggcacctatc tcagcgatct gtctatttcg   3355

ttcatccata gttgcctgac tccccgtcgt gtagataact acgatacggg agggcttacc   3415

atctggcccc agtgctgcaa tgataccgcg agacccacgc tcaccggctc cagatttatc   3475

agcaataaac cagccagccg gaagggccga gcgcagaagt ggtcctgcaa ctttatccgc   3535

ctccatccag tctattaatt gttgccggga agctagagta agtagttcgc cagttaatag   3595

tttgcgcaac gttgttgcca ttgctgcagg catcgtggtg tcacgctcgt cgtttggtat   3655

ggcttcattc agctccggtt cccaacgatc aaggcgagtt acatgatccc ccatgttgtg   3715

caaaaaagcg gttagctcct tcggtcctcc gatcgttgtc agaagtaagt tggccgcagt   3775

gttatcactc atggttatgg cagcactgca taattctctt actgtcatgc catccgtaag   3835

atgcttttct gtgactggtg agtactcaac caagtcattc tgagaatagt gtatgcggcg   3895

accgagttgc tcttgcccgg cgtcaacacg ggataatacc gcgccacata gcagaacttt   3955

aaaagtgctc atcattggaa aacgttcttc ggggcgaaaa ctctcaagga tcttaccgct   4015

gttgagatcc agttcgatgt aacccactcg tgcacccaac tgatcttcag catcttttac   4075

tttcaccagc gtttctgggt gagcaaaaac aggaaggcaa aatgccgcaa aaaagggaat   4135

aagggcgaca cggaaatgtt gaatactcat actcttcctt tttcaatatt attgaagcag   4195

acagttttat tgttcatgat gatatatttt tatcttgtgc aatgtaacat cagagatttt   4255

gagacacaac gtggctttgt tgaataaatc gaacttttgc tgagttgaag gatcagatca   4315

cgcatcttcc cgacaacgca gaccgttccg tggcaaagca aaagttcaaa atcaccaact   4375

ggtccaccta caacaaagct ctcatcaacc gtggctccct cactttctgg ctggatgatg   4435

gggcgattca ggcctggtat gagtcagcaa caccttcttc acgaggcaga cctca        4490


<210> SEQ ID NO 2
<211> LENGTH: 85
<212> TYPE: PRT
<213> ORGANISM: Artificial Sequence
<220> FEATURE:
<223> OTHER INFORMATION: Description of Artificial Sequence: vector
      pCorrectClone including modified gvpA sequence from Anabaena
      flos-aquae

<400> SEQUENCE: 2

Met Gly Thr Pro Gly Glu Phe Asp Ile Ser Ser Gly Arg Val Asp Ala
  1               5                  10                  15

Val Glu Lys Thr Asn Ser Ser Ser Ser Leu Ala Glu Val Ile Asp Arg
             20                  25                  30

Ile Leu Asp Lys Gly Ile Val Ile Asp Ala Trp Val Arg Val Ser Leu
         35                  40                  45

Val Gly Ile Glu Leu Leu Ala Ile Glu Ala Arg Ile Val Ile Ala Ser
     50                  55                  60

Val Glu Thr Tyr Leu Lys Tyr Ala Glu Ala Val Gly Leu Thr Gln Ser
 65                  70                  75                  80

Ala Ala Val Pro Ala
                 85


<210> SEQ ID NO 3
<211> LENGTH: 101
<212> TYPE: DNA
<213> ORGANISM: Artificial Sequence
<220> FEATURE:
<223> OTHER INFORMATION: Description of Artificial Sequence: synthetic
      primer
```

-continued

```
<400> SEQUENCE: 3

gattaacttt ataaggagga tataccatgg gtaccccggg tgaattcgat atctcgagcg      60

gccgcgtcga cgcagttgaa aaaaccaatt cttcctccag c                        101

<210> SEQ ID NO 4
<211> LENGTH: 35
<212> TYPE: DNA
<213> ORGANISM: Artificial Sequence
<220> FEATURE:
<223> OTHER INFORMATION: Description of Artificial Sequence: synthetic
      primer

<400> SEQUENCE: 4

tctagataat taaaaaaagc agaaccaata tcagg                                35
```

CLONING VECTOR

Figure 1:
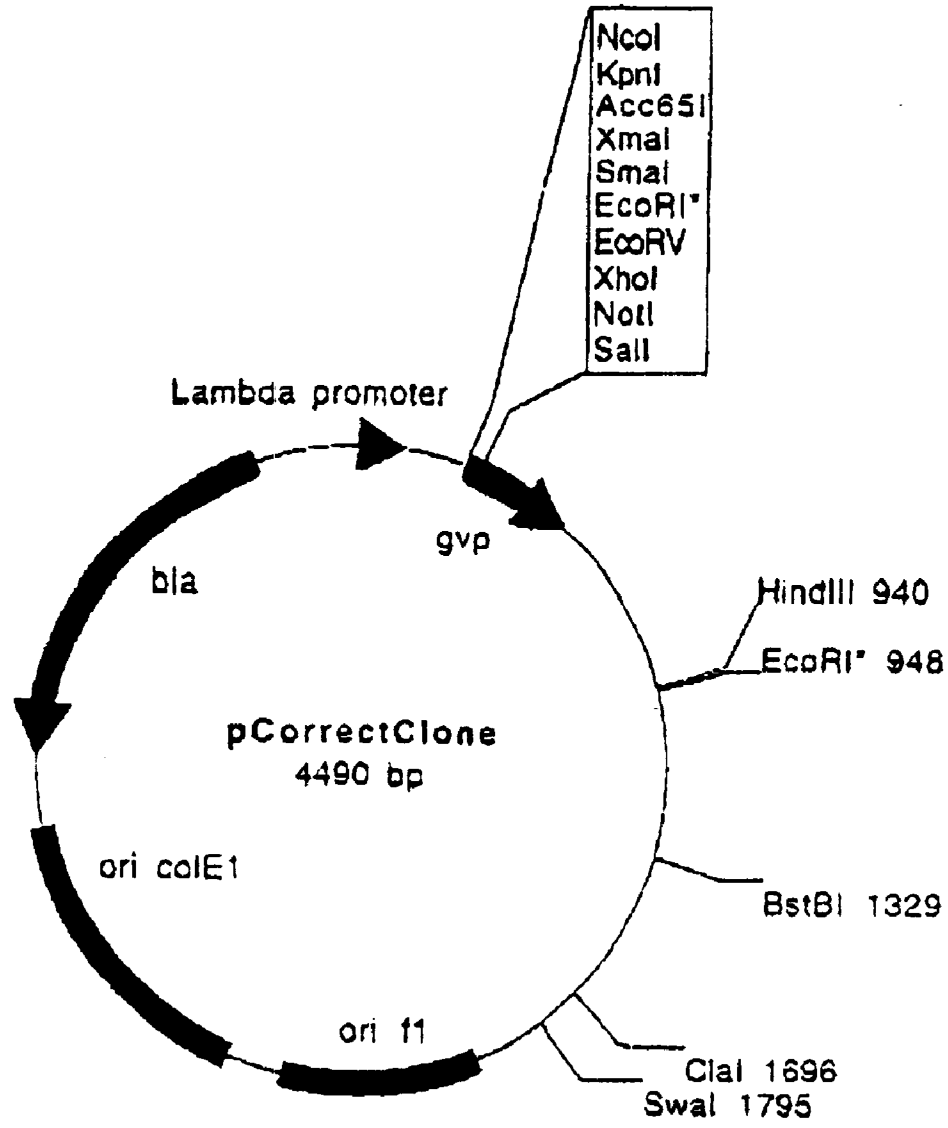

The present invention relates to cloning vectors, cloning methods and cloning kits. More particularly, the present invention relates to a cloning vector comprising a nucleic acid sequence encoding a polypeptide which when expressed is lethal for a bacterial host cell and at least one cloning site wherein the insertion of a foreign nucleic acid insert in the cloning site causes a disruption of the expression of the lethal polypeptide.

For many molecular biology applications DNA fragments are inserted into cloning vectors, transformed into bacterial cells and plated onto selection medium for individual colony isolation. Frequently, however, problems occur because host cells containing the desired recombinant vector containing the foreign DNA are only obtained with low frequency, particularly when blunt-ended DNA fragments are inserted into the vectors.

U.S. Pat. No. 5,843,656 discloses a recombinant clone selection system for expression in a host cell comprising a repressor gene coding for a repressor, a promoter for promoting the expression of the repressor gene, a restriction endonuclease cleavage insertion site located within the repressor gene or its associated promoter such that when a foreign nucleic acid is inserted at the insertion site, expression of the repressor gene is insertionally inactivated, a surface-expressed moiety gene and an operator functionally linked to the expression of the surface-expressed moiety gene such that when the repressor is bound to the operator expression of the surface-expressed moiety gene is repressed. Transformed host cells containing the foreign nucleic acids may be isolated via the expression of the surface-expressed moiety gene. The method, however, is elaborate and requires compared to standard cloning methods a considerably larger amount of time.

U.S. Pat. No. 6,891,687 claims a vector for cloning a DNA sequence into adenylate-cyclase-positive host cells, the vector containing a selection gene comprising a modified CAP gene which codes for a modified CAP protein with reduced DNA binding specifity compared to a wild-type CAP protein, the expression of which selection gene is lethal in a portion of the host cells, wherein a restriction site for the DNA sequence is located within the selection gene and upon insertion of the DNA sequence at the restriction site, the expression of the selection gene in the host cells is prevented, wherein the modified CAP gene is modified such that the glutamic acid at position 181 of the wild-type CAP protein is substituted by glutamine. A disadvantage of this system is that it is restricted to adenylate-cyclase-positive host cells.

The problem underlying the present invention was thus to provide a new cloning system avoiding the disadvantages of the prior art. This problem is solved by providing a cloning vector comprising (a) a nucleic acid sequence encoding a polypeptide which is lethal for a bacterial host cell wherein the nucleic acid sequence is operatively linked to a regulatable expression control sequence, wherein said polypetide is selected from the *Anabaena flos-aquae* GvpA protein or a polypeptide which is homologous thereto, and (b) at least one cloning site wherein insertion of a foreign nucleic acid insert in the cloning site causes a disruption of the expression of the lethal polypeptide.

The cloning vector of the present invention is a tool for high-efficient cloning of DNA fragments and high-level expression of proteins in bacterial hosts, e.g. *E. coli.* The positive selection that makes the cloning so easy is based on the nucleic acid sequence encoding for a small protein which is located on the vector. Over expression of this polypeptide is toxic for *E. coli* and leads to cell death of bacteria carrying the nucleic acid sequence. When a DNA fragment is inserted into the cloning site of the vector, which may be located within the protein coding sequence or between the expression control sequence and the protein coding sequence, the expression of the lethal gene is disrupted. Thus, only transformants with insert-containing vectors will grow, whereas transformants containing the vector without insert cannot grow. The vector is particularly useful for the construction of nucleic acid, e.g. cDNA or genomic libraries, e.g. for sequencing projects and the cloning of PCR products.

Preferably, the vector of the present invention is a bacterial vector, i.e. it contains nucleic acid sequences which allow a propagation in prokaryotic host cells, particularly *E. coli.* Thus, a vector comprises at least one origin of replication which may be a bacterial origin of replication such as colE1 or p15A or a bacteriophage origin such as the f1 origin. In a particularly preferred embodiment, the vector comprises at least two origins of replication, wherein at least one origin is a bacterial origin and at least one orgin is a bacteriophage origin. Furthermore, it is preferred that the vector comprises a selection marker gene, which allows selection on transformants containing the vector. The selection marker gene may be an antibiotic resistance gene such as the ampicillin, kanamycin or tetracyclin resistance gene, In a particularly preferred embodiment the antibiotic resistance gene is the ampicillin resistance gene, i.e. the beta-lactamase gene.

An essential feature of the present invention is the presence of a nucleic acid sequence in the vector encoding a polypeptide which is conditionally lethal for the bacterial host cell. This nucleic acid sequence is operatively linked to a suitable expression control sequence, which is regulatable in a manner which allows propagation of the vector under conditions, wherein the expression control sequence is substantially inactive. Preferably, the expression control sequence is regulatable by a repressor. A specific example is a phage lambda promoter, e.g. the $P_L$ or $P_R$ promoter including operator sequences which allow effective binding of lambda repressor and thus substantially inactivating the expression control sequence under appropriate conditions, e.g. in a host cell, which produces the lambda repressor in sufficient amount. Furthermore, the expression control sequence may comprise a translation enhancer, e.g. the T7 translation enhancer to allow effective translation of any heterologous nucleic acid sequence which is inserted into the cloning site.

The vector may also contain at least one nucleotide sequence which is complementary to a sequencing and/or amplification primer. These complementary nucleotide sequences are preferably located adjacent to the cloning site and thus allow efficient sequencing and/or amplification of any foreign nucleic acid fragment which is inserted in the cloning site. Moreover, the vector may be a shuttle vector, which allows propagation in different host cells, e.g. it may additionally comprise nucleic acid sequences which allow a propagation in eukaryotic host cells.

The lethal polypeptide is selected from the *Anabaena flos-aquae* GvpA protein (Genbank accession No. M32060) or a polypeptide homologous thereto, which may be a protein from *Fremyella diplosiphon* (Genbank accession No. P07060), a protein from Calothrix (Genbank accession No. AAB23332), a protein from Pseudoanabaena spec. (Genbank accesssion No. P22453), a protein from *Planktothrix rubescens* (Genbank accession No. CAB59543 and CAB59546), a protein from *Aphanizomenon flos-aquae*

(Genbank accession No. SVFZ), a protein from Microcystis spec. (Genbank accession No. P08412), a protein from *Oscillatoria agardhii* (Genbank accession No. P80996), a protein from *Thiocapsa pendens* (Genbank accession No. P80998), a protein from *Amoebobacter pendens* (Genbank accession No. AAB23337), a protein from *Bacillus megaterium* (Genbank accession No. AAC38419, AAC38416 and AF053765), a protein from Spirulina spec. (Genbank accession No. P80997), a protein from *Haloferax mediterranei* (Genbank accession No. P23761 and Q02235), a protein from *Halobacterium halobium* (Genbank accession No. P08959, S07323, P08959 and P24374), a protein from *Dactylococcopsis salina* (Genbank accession No. AAB23336), a protein from *Halorubrum vacuolatum* (Genbank accession No. CAA69881), a protein from *Streptomyces coelicolor* (Genbank accession No. CAB61167, CAB61172 and CAA22042) and a protein from *Halobacterium salinarium* (Genbank accession No. P33956).

The present invention encompasses a nucleic acid sequence encoding a conditionally lethal polypeptide which is homologous to the GvpA protein from *Anabaena flos-aquae*. The homologous polypeptide preferably has an identity of more than 60%, preferably more than 75% and particulary preferred more than 90% to the GvpA protein and is, when expressed under non-repressed conditions, lethal for a bacterial host.

The identity is determined on protein level as follows:

$$I = \frac{n}{L},$$

wherein

I represents the identity in percent n represents the number of different amino acids between a test sequence and the GvpA sequence and L is the length of the GvpA sequence to be compared with a test sequence.

The nucleic acid sequence encoding the *Anabaena flos-aquae* GvpA protein and the corresponding polypeptide sequence are described in Genbank accession No. M322060. In a particularly preferred embodiment of the present invention the lethal polypeptide is encoded by (a) the nucleotide sequence encoding the *Anabaena flos-aquae* GvpA protein, (b) a nucleotide sequence corresponding to the sequence of (a) within the scope of the degeneracy of the genetic code or (c) a nucleotide sequence hybridizing under stringent conditions with the sequence of (a) and/or (b).

The term "hybridization under stringent conditions" is defined according to Sambrook et al., Molecular Cloning, A Laboratory Manual, Cold Spring Harbor, Laboratory Press (1989), 1.101–1.104. Preferably, hybridization under stringent conditions means that after washing for 1 h with 1×SSC and 0.1% SDS at 50° C., preferably at 55° C., more preferably at 62° C. and most preferably at 68° C., particularly for 1 h in 0.2×SSC and 0.1% SDS at 50° C., preferably at 55° C., more preferably at 62° C. and most preferably at 68° C., a positive hybridization signal is observed. A nucleotide sequence which hybridizes under the above washing conditions with the nucleotide sequence coding for the gvpA gene of *Anabaena flos-aquae* (Genbank accession No. M32060) or a nucleotide sequence corresponding thereto in the scope of the degeneracy of the genetic code is encompassed by the present invention.

The vector also comprises a cloning site which allows the insertion of foreign nucleic acid fragments. The position of the cloning site is such that insertion of foreign nucleic acid fragments causes a disruption, particularly a substantially complete inactivation of the expression of the lethal polypeptide. Thus, the cloning site may be located within the nucleic acid sequence encoding the lethal polypeptide or between the expression control sequence and the start of the polypeptide sequence. More preferably, the cloning site is located adjacent to the 5'-region of the coding sequence. Further, it is preferred that the cloning site is a multiple cloning site comprising recognition sites for a plurality of restriction enzymes, which e.g. may be selected from the group consisting of NcoI, KpnI, Acc651, XmaI, SmaI, SmaI, EcoRI, XhoI, NotI, EcoRV and SalI.

A further subject matter of the present invention is a cloning method comprising the steps:

(a) providing a cloning vector as described above, (b) inserting a foreign nucleic acid molecule, which may be a blunt-ended DNA fragment, e.g. a PCR product, into the cloning site, wherein a vector containing the foreign nucleic acid molecule is obtained, (c) transforming competent bacterial host cells, e.g. *E. coli* cells, with the vector obtained in step (b) and (d) recovering transformed bacterial host cells which harbor the vector containing the foreign nucleic acid molecule.

Step (d) may comprise the culturing of transformed host cells under appropriate selection conditions, e.g. in an antibiotic containing medium, preferably a solid medium, and characterizing positive clones. When carrying out this method it was found that at least 90% of recovered transformed host cells harbor the vector containing the foreign nucleic acid molecule.

Moreover, the present invention relates to a reagent kit for cloning and optionally expressing foreign nucleic acid molecules comprising the vector as described above and further reagents. These further reagents may be selected from enzymes such as DNA ligase and/or restriciton enzymes, e.g. T4 DNA ligase and restriction endonuclease SmaI, buffers, e.g. enzyme buffers and sequencing or amplification primers. Furthermore, the kit may comprise competent bacterial host cells, e.g. *E. coli* cells.

Further, the invention shall be explained by the following figures and examples:

FIG. 1 shows a schematic image of the vector pCorrectClone according to the Invention.

SEQ ID NO 1 shows the nucleotide sequence of the vector pCorrectClone including the gvpA sequence from *Anabaena flos-aquae,* which has been modified to include a multiple cloning site. The modified gvpA gene begins at position 251 (ATG) and ends at position 505 (GCT).

EXAMPLE 1

By using the primers A (SEQ ID NO: 3)(5'-GAT TAA CTT TAT AAG GAG GAT ATA CCA TGG GTA CCC CGG GTG AAT TCG ATA TCT CGA GCG GCC GCG TCG ACG CAG TTG AAA AAA CCA ATT CTT CCT CCA GC-3') and B (5'-TCT AGA TAA TTA AAA AAA GCA GAA CCA ATA TCA GG-3') SEQ ID NO: 4) a PCR-amplification of the gvpA (gas-vesicle protein A) gene was produced from *Anabaena flos-aquae* strain CCAP14103/13F. The nucleotide sequence of the gene and the corresponding polypeptide is disclosed under Genbank accession No. M32060.

The primer A contains the T7 gene 10 translation enhancer and successively multiple cloning site with recognition sites for the restriction enzymes NcoI, KpnI, Acc651, XmaI, SmaI, EcoRI, EcoRV, XhoI, NotI and SalI as well as the 5'-region of the gvpA gene.

The PCR product was cloned into the EcoNI site of the vector pSF1e. This vector was obtained by cleaving the vector pSF1 (Eur. J. Biochem. 179 (1989), 399–404) with EcoRI and religation with concomittant deletion of the ssb-DNA fragment.

More than 30 clonings were performed in the resulting vector (pCorrectClone). in which different DNAs were cloned into all sections of the multiple cloning site. The functionality of the conditional lethal system was given in every case. The nucleic acid sequence of pCorrectClone is depicted in SEQ ID NO 1.

Thus, upon cloning of a 2.1 KB Kpnl DNA fragment (sticky ends). Into the Kpnl site of the multiple cloning site or a 2.0 KB PCR product (blunt ends), respectively, into the Smal site of the multiple cloning site more than 95% recombinant clones each are obtained.

What is claimed is:

1. An *Escherichia coli* cloning vector comprising
   (a) a nucleic acid sequence encoding a modified polypeptide which is lethal for an *E. coli* cell operatively linked to a regulatable expression control sequence, wherein said polypeptide is selected from the *Anabaena flos-aquae* GvpA protein (Genbank accession No. M32060) or a polypeptide homologous thereto, wherein said homologous polypeptide has an identity of more than 90% to the GvpA protein, and
   (b) at least one cloning site comprising a multiple non-naturally occurring cloning site located within the sequence encoding the modified protein, wherein insertion of a foreign nucleic acid insert in the cloning site causes a disruption of the expression of the lethal polypeptide;
   wherein the lethal polypeptide is encoded by (i) the nucleotide sequence encoding the *Anabaena flos-aquea* GvpA protein (Genbank accession No. M32060), (ii) a nucleotide sequence corresponding to the sequence of (i) within the scope of the degeneracy of the genetic code or (iii) a nucleotide sequence hybridizing with the sequence of (i) and/or (ii) under stringent conditions which comprise washing for 1 hour with 1.0×SSC and 0.1% SDS at 50° C.

2. The vector of claim 1, further comprising a selection marker gene.

3. The vector of claim 1 wherein the lethal polypeptide is selected from the *Anabaena flos-aquae* GvpA protein (Genbank accession No. M32060), a protein from *Fremyella diplosiphon* (Genbank accession No. P07060), a protein from Calothrix (Genbank accession No. AAB23332), a protein from Pseudoanabaena spec. (Genbank accesssion No. P22453), a protein from *Planktothrix rubescens* (Genbank accession No. CAB59543 and CAB59546), a protein from *Aphanizomenon flos-aquae* (Genbank accession No. SVFZ), a protein from Microcystis spec. (Genbank accession No. P08412), a protein from *Oscillatoria agardhii* (Genbank accession No. P80996), a protein from *Thiocapsa pendens* (Genbank accession No. P80998), a protein from *Amoebobacter pendens* (Genbank accession No. AAB23337), a protein from *Bacillus megaterium* (Genbank accession No. AAC38419, AAC38416 and AF053765), a protein from Spirulina spec. (Genbank accession No. P80997), a protein from *Haloferax mediterranei* (Genbank accession No. P23761 and Q02235), a protein from *Halobacterium halobium* (Genbank accession No. P08969, S07323, P08959 and P24374), a protein from *Dactylococcopsis salina* (Genbank accession No. AAB23336), a protein from *Halorubrum vacuolatum* (Genbank accession No. CAA69881), a protein from *Streptomyces coelicolor* (Genbank accession No. CAB61167, CAB61172 and CAA22042) and a protein from *Halobacterium salinarium* (Genbank accession No. P33956).

4. The vector of claim 1 wherein the multiple cloning site comprises recognition sites for restriction enzymes selected from the group consiting of Ncol, Kpnl, Acc65I, Xmal, Smal, EcoRI, EcoRV, XhoI, Notl and SalI.

5. The vector of claim 1 wherein the expression control sequence is regulatable by a repressor.

6. The vector of claim 5 wherein the expression control sequence comprises a phage λ promoter.

7. The vector of claim 1 wherein the expression control sequence comprises a translation enhancer.

8. The vector of claim 1 comprising at least one bacterial origin.

9. The vector of claim 8 comprising at least one bacterial origin and at least one bacteriophage origin.

10. The vector of claim 1 further comprising at least one nucleotide sequence which is complementary to a sequencing and/or amplification primer.

11. The vector of claim 1 further comprising nucleic acid sequences which allow a propagation in eukaryotic host cells.

12. A cloning method comprising the steps:
    (a) providing the vector of claim 1,
    (b) inserting a foreign nucleic acid molecule into the cloning site, wherein a vector containing the foreign nucleic acid molecule is obtained,
    (c) transforming competent bacterial host cells with the vector obtained in step (b) and
    (d) recovering transformed bacterial host cells which harbor the vector containing the foreign nucleic acid molecule.

13. The method of claim 12 wherein the host cells are *E. coli* cells.

14. The method of claim 13 wherein at least 90% of recovered transformed host cells harbor the vector containing the foreign nucleic acid molecule.

15. A reagent kit for cloning comprising the vector of claim 1 and further reagents.

16. The kit of claim 15 wherein the further cloning reagents are selected from enzymes, buffers and sequencing or amplification primers.

17. The kit of claim 16 wherein the enzymes are selected from T4 DNA ligase and restriction endonuclease SmaI.

18. The kit of claim 15 further comprising competent *E. coli* cells.

19. An *Escherichia coli* cloning vector comprising (a) a nucleic acid sequence encoding a modified polypeptide which is lethal for an *E. coli* cell operatively linked to a regulatable expression control sequence, wherein said polypeptide comprises SEQ ID NO 2, and (b) at least one cloning site comprising a multiple cloning site, wherein insertion of a foreign nucleic acid insert in the cloning site causes a disruption of the expression of the lethal polypeptide.

* * * * *